United States Patent
Kusumegi et al.

(10) Patent No.: US 9,166,241 B2
(45) Date of Patent: Oct. 20, 2015

(54) ENZYME ELECTRODE, AND BIO FUEL CELL EQUIPPED THEREWITH

(75) Inventors: Takahiro Kusumegi, Toyota (JP); Noriko Hayashi, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 234 days.

(21) Appl. No.: 13/697,722

(22) PCT Filed: May 5, 2011

(86) PCT No.: PCT/IB2011/001242
§ 371 (c)(1),
(2), (4) Date: Nov. 13, 2012

(87) PCT Pub. No.: WO2011/145000
PCT Pub. Date: Nov. 24, 2011

(65) Prior Publication Data
US 2013/0059212 A1     Mar. 7, 2013

(30) Foreign Application Priority Data
May 17, 2010   (JP) ................................. 2010-113083

(51) Int. Cl.
*H01M 8/16*    (2006.01)
*C12Q 1/00*    (2006.01)
*H01M 4/90*    (2006.01)

(52) U.S. Cl.
CPC ................. *H01M 8/16* (2013.01); *C12Q 1/001* (2013.01); *H01M 4/9008* (2013.01); *H01M 4/9075* (2013.01); *Y02E 60/527* (2013.01)

(58) Field of Classification Search
CPC ........................................................ H01M 8/16
USPC ........................................................ 429/401
See application file for complete search history.

(56) References Cited

U.S. PATENT DOCUMENTS

| 4,820,399 A | 4/1989 | Senda et al. |
| 2009/0047550 A1* | 2/2009 | Kakuta et al. ................... 429/12 |
| 2011/0039165 A1 | 2/2011 | Sugiyama et al. |
| 2011/0136022 A1 | 6/2011 | Matsumoto et al. |

FOREIGN PATENT DOCUMENTS

| JP | 2007-012281 A | 1/2007 |
| JP | 2008-177088 A | 7/2008 |
| JP | 2009-048846 A | 3/2009 |
| JP | 2009-515302 A | 4/2009 |
| JP | 2009-140760 A | 6/2009 |
| JP | 2009-140781 A | 6/2009 |
| JP | 2009-245930 A | 10/2009 |
| JP | 2011-018635 A | 1/2011 |
| WO | 2007/056666 A2 | 5/2007 |

* cited by examiner

*Primary Examiner* — Kenneth Douyette
*Assistant Examiner* — James Lee
(74) *Attorney, Agent, or Firm* — Sughrue Mion, PLLC

(57) ABSTRACT

An enzyme electrode having an electroconductive base member, an oxidoreductase and an electron mediator has at least a portion (a) in which the oxidoreductase is immobilized on the electroconductive base member, and a portion (b) in which the electron mediator is immobilized on the electroconductive base member but the oxidoreductase is not immobilized on the electroconductive base member. A bio fuel cell having the enzyme electrode as at least one of an anode and a cathode allows optimization of a reaction condition of each one of a plurality of reaction steps, including an "enzymatic reaction", an "electron transfer reaction", etc. Thus, the bio fuel cell provides high output.

7 Claims, 3 Drawing Sheets

ENZYME ELECTRODE, AND BIO FUEL CELL EQUIPPED THEREWITH

BACKGROUND OF THE INVENTION

1. Field of the Invention

The invention relates to an enzyme electrode, and to a bio fuel cell that employs an enzyme electrode as at least one of the anode electrode and the cathode electrode.

2. Description of the Related Art

Recently, interest in fuel cells as a countermeasure to environmental issues and natural resource issues is increasing. A fuel cell converts chemical energy directly into electric energy by supplying a fuel and an oxidant to two electrically connected electrodes so that the fuel is electrochemically oxidized. The fuel cell, which electrochemically extracts energy, is not subject to the restrictions of the Carnot cycle, in contrast to thermal electric power generation, and therefore exhibits high energy conversion efficiency. Conventional fuel cells include solid polymer electrolyte fuel cells (PEFC), alkaline electrolyte fuel cells (AFC), phosphoric acid fuel cells (PAFC), etc. Such fuel cells often use platinum (Pt) as a catalyst. However, platinum is very costly, which is an impediment to its widespread use in fuel cells.

Recently, a bio fuel cell is drawing attention as a type of fuel cell that does not use platinum as a catalyst. The bio fuel cell is a fuel cell to which a metabolic mechanism of living organisms is applied. An example of the construction of the bio fuel cell is as follows. First, an oxidoreductase, that is, an oxidation-reduction enzyme, is immobilized on the anode electrode. In order to obtain high output, the bio fuel cell system often contains a coenzyme that is needed for the enzymatic reaction of the oxidoreductase and an electron mediator that receives electrons produced by the enzymatic reaction and transfers the electrons to the electrode. Then, the fuel cell extracts electrons and protons (H+) from a fuel, such as glucose or the like, through the enzymatic reaction. The extracted protons move to the cathode electrode via a proton conductor. In the cathode electrode, protons, electrons and oxygen that is taken in from the atmosphere or the like react to produce water.

With regard to the bio fuel cell as described above, various studies are being conducted in order to increase the power output. For example, Japanese Patent Application Publication No. 2009-140760 (JP-A-2009-140760) describes a fuel cell that includes an anode electrode on which an enzyme, a coenzyme and an electron mediator are immobilized, wherein at least one of the coenzyme and the electron mediator is also added in a fuel solution. Published Japanese Translation of PCT Application No. 2009-515302 (JP-A-2009-515302) describes a fuel cell in which a hydrophobic denatured polysaccharide that is permeable to fuel and an electron mediator is used as a substance for immobilizing an enzyme to the anode electrode.

However, the power output of conventional bio fuel cells is still unsatisfactory. A conceivable reason for this is that in the bio fuel cells, extraction of energy requires a plurality of reaction steps, including an "enzymatic reaction", an "electron transfer reaction", etc. The factors involved in these reactions include not only the oxidoreductase but also the coenzyme and the electron mediator, and some of the conditions suitable for the different reaction steps. Thus, optimization for each reaction is difficult.

SUMMARY OF THE INVENTION

Accordingly, the present inventors have considered the construction of an electrode that optimizes the conditions for individual reactions, such as "the enzymatic reaction", "the electron transfer reaction", etc., and have come to an idea of an electrode construction in which each of electrodes is provided that serve for a specific one of the different reactions.

A first aspect of the invention is an enzyme electrode having an electroconductive base member, an oxidoreductase and an electron mediator, and having at least a portion (a) in which the oxidoreductase is immobilized on the electroconductive base member, and a portion (b) in which the electron mediator is immobilized on the electroconductive base member but the oxidoreductase is not immobilized on the electroconductive base member.

In addition, the enzyme electrode in accordance with the first aspect may have a structure in which the portion (a) and the portion (b) continuously alternate with each other.

In the enzyme electrode in accordance with the first aspect, a shortest distance between the portion (a) and the portion (b) may be less than or equal to 0.5 mm, in at least a portion of the enzyme electrode.

A second aspect of the invention is a fuel cell characterized by having the enzyme electrode in accordance with the first aspect as at least one of an anode electrode and a cathode electrode.

In the fuel cell in accordance with the second invention,
the enzyme electrode may be provided as the anode electrode, and
nicotinamide adenine dinucleotide may be contained in a fuel solution as a coenzyme that assists the oxidoreductase, and
a reduction starting potential of the electron mediator may be greater than or equal to −0.32 V.

In addition, in the fuel cell in accordance with the second aspect of the invention, the enzyme electrode may be provided as the cathode electrode, and nicotinamide adenine dinucleotide may be contained in a fuel solution as a coenzyme that assists the oxidoreductase, and a reduction starting potential of the electron mediator may be less than or equal to 1.2 V.

In the fuel cell employing the enzyme electrode of the invention, since in the enzyme electrode, a portion in which the oxidoreductase is immobilized and a portion in which the electron mediator is immobilized but the oxidoreductase is not immobilized are separate from each other, the conditions for the individual reactions, such as the enzymatic reaction, the electron transfer reaction, etc., are improved, so that a considerably improved output can be achieved than in a fuel cell that employs an enzyme electrode according to the related art.

BRIEF DESCRIPTION OF THE DRAWINGS

The features, advantages, and technical and industrial significance of this invention will be described below with reference to the accompanying drawings, in which like numerals denote like elements, and wherein.

DETAILED DESCRIPTION OF EMBODIMENTS

Figure 1:
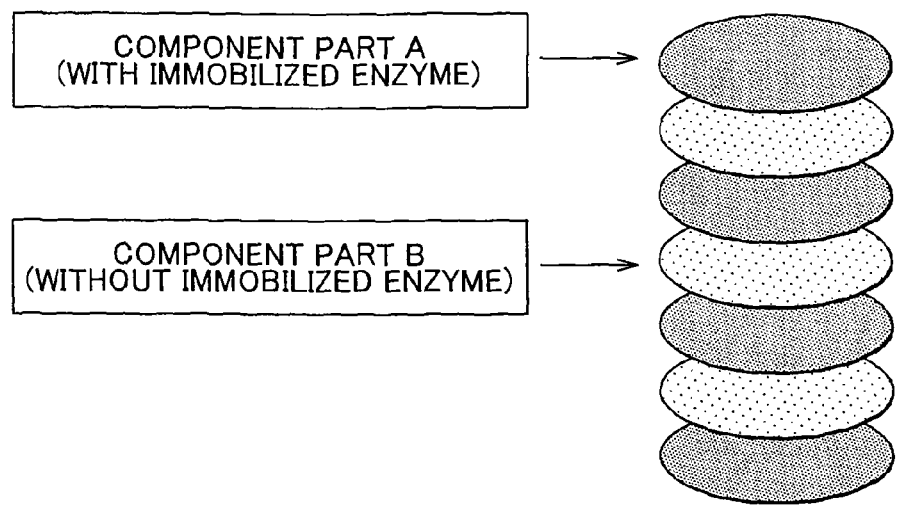
FIG. 1 is a diagram of the structure of an enzyme electrode according to one embodiment of the invention.

An enzyme electrode in accordance with an embodiment of the invention is characterized by including an electroconductive base member, an oxidoreductase and an electron mediator, and by having at least a first portion (a) in which the oxidoreductase is immobilized on the electroconductive base member, and a second portion (b) in which the electron mediator is immobilized on the electroconductive base member but the oxidoreductase is not immobilized on the electroconductive base member. In the first portion (a), the electron mediator as well as the oxidoreductase may also be immobilized on the electroconductive base member.

Conventional electroconductive base members may be used as the electroconductive base member, including, for example, electroconductive carbon materials such as graphite, carbon black, active carbon, etc., metals such as gold, platinum, etc., and so on. Specifically, suitable electroconductive base members include carbon paper, glassy carbon, HOPG (highly oriented pyrolytic graphite), a carbon fiber mat impregnated with a carbon slurry that contains a porous carbon, a solvent and a polymer, etc.

As the oxidoreductase, for example, a dehydrogenase, an oxidase, etc., may be used. Suitable oxidoreductases include, for example, glucose dehydrogenase (GDH), fructose dehydrogenase (FDH), alcohol dehydrogenase (ADH), aldehyde dehydrogenase, glucose oxidase (GOD), alcohol oxidase (AOD), aldehyde oxidase, formic acid dehydrogenase, formic acid oxidase, diaphorase, multicopper oxidase, etc. The oxidoreductase used in the invention may be a single species thereof, or may also be a combination of two or more species thereof.

The enzyme electrode of the invention may be used as both an anode electrode and a cathode electrode of a fuel cell. If the enzyme electrode of the invention is used as an anode electrode, the oxidoreductase is an enzyme that oxidizes a substrate. However, if the enzyme electrode of the invention is used as a cathode electrode, the oxidoreductase is an enzyme that reduces a substrate.

In the invention, the electron mediator is a substance that donates electrons to and accepts electrons from an enzyme or a coenzyme and is also able to donate electrons to and accepts electrons from the electroconductive base member. Examples of compounds that can be used as the electron mediator include: metal complexes (ferrocene, alkali metal ferrocyanides such as potassium ferricyanide, lithium ferricyanide, sodium ferricyanide, and their alkyl substitution products (methyl substitution products, ethyl substitution products, propyl substitution products, etc.), potassium octacyano tangstate, etc.) whose central metals are selected from among metal elements such as Os, Fe, Ru, Co, Cu, Ni, V, Mo, Cr, Mn, Pt, W, etc., and ions of these metal elements; quinones such as quinone, benzoquinone, anthraquinone, naphthoquinone, etc.; heterocyclic compounds such as viologen, methyl viologen, benzyl viologen, phenazine metsulfate, phenazine etsulfate, bipyridine and their derivatives, etc.; and 2,6-dichlorophenolindophenol, methylene blue, potassium β-naphthoquinone-4-sulfonate, vitamin K, etc.

The electrode potential at the enzyme electrode in which the electron transfer between the enzyme and the electrode is performed via the electron mediator, depends on the oxidation-reduction potential of the electron mediator. Hence, as for the anode electrode (substrate oxidation type enzyme electrode), lower oxidation starting potentials of the electron mediator within a range where the oxidation starting potential is higher than the oxidation-reduction potential of the enzyme or coenzyme that directly transfers electrons to the electron mediator cause smaller energy losses, and achieve higher voltages in cell assemblies, and therefore are more preferable. However, as for the cathode electrode (substrate reduction type enzyme electrode), higher reduction starting potentials of the electron mediator within a range where the reduction starting potential is lower than the oxidation-reduction potential of the enzyme or coenzyme that directly receives electrons from the electron mediator cause smaller energy losses, and achieve higher voltages in cell assemblies, and therefore are more preferable.

For example, if the anode uses NAD/NADH as a coenzyme, it is preferable to use an electron mediator that has a reduction starting potential higher than or equal to $-0.32$ V. If the substrate at the cathode is oxygen, it is preferable to use an electron mediator that has reduction starting potential lower than or equal to 1.2 V. A suitable electron mediator may be selected in accordance with conditions regarding fuel and the like.

The oxidoreductase may be immobilized on an electroconductive base member using a polymer and a crosslinking agent. Examples of suitable polymers that may be used to immobilize the enzyme include polyvinyl imidazole, polyallylamine, polyamino acid (poly-L-lysine, etc.), polypyrrole, polyacrylic acid, polyvinyl alcohol, polyethyleneimine, etc. Suitable crosslinking agents include polyethyleneglycol diglycidyl ether, glutaraldehyde, etc. Specific examples of a combination of a polymer and a crosslinking agent used to immobilize the enzyme include a combination of poly-L-lysine and glutaraldehyde at a weight ratio ranging from 5:1 to 80:1.

Examples of the enzyme electrode that has at least a first portion (a) in which the oxidoreductase is immobilized on the electroconductive base member and a second portion (b) in which the electron mediator is immobilized on the electroconductive base member but the oxidoreductase is not immobilized on the electroconductive base member include, for example, an electrode constructed of a combination of a component part A, in which an oxidoreductase is immobilized on an electroconductive base member, and a component part B, in which an electron mediator is immobilized on an electroconductive base member (but in which an oxidoreductase is not provided), an electrode made up of a single electroconductive base member that has a first portion A, in which an oxidoreductase is immobilized, and a second portion B, in which an electron mediator is immobilized (but in which an oxidoreductase is not provided), the portion A and the portion B being formed by separate steps from each other. The electrode of the invention may employ the former configuration combining the component part A and the component part B for ease in manufacture or the like. Preferably, the enzyme electrode of the invention has a structure in which the component part A and the component part B or the portion A and the portion B continuously alternate with each other. The term "continuously alternate with each other" refers to, for example, a structure in which a repetition unit made up of, for example, the component parts A and B, is repeated two or more times.

Figure 2:
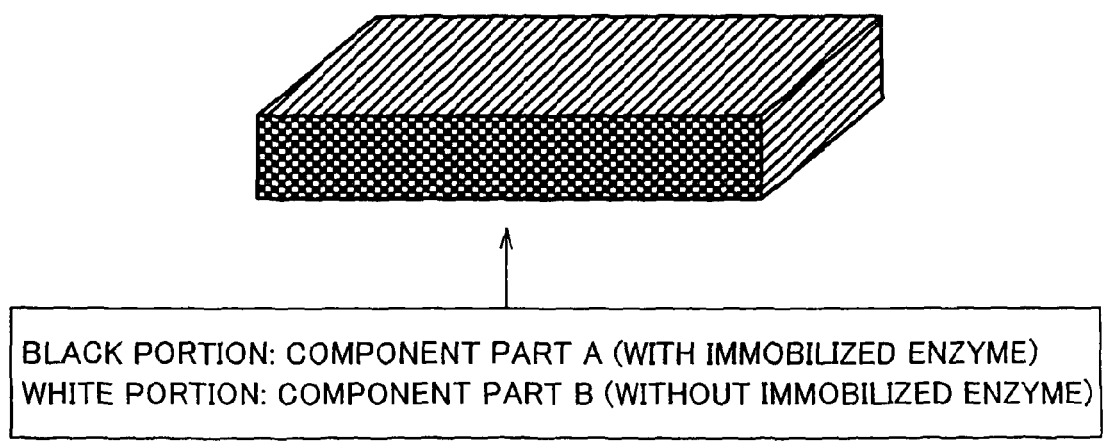
FIG. 2 is a diagram of an alternative structure of the enzyme electrode.

FIG. 1 and FIG. 2 show example configurations of the component parts A and B combined which have a structure in which the component part A and the component part B continuously alternate with each other. In the example shown in FIG. 1, component parts A and component parts B are thin circular plates, and are alternately gathered to form a layer structure. The shape of the thin plates is not limited to a circular shape, but may be any suitable shape, such as an ellipse, a square, a rectangle, any other polygon, etc. according to need. In addition, the number of layers made up of component parts A and component parts B can also be an arbitrary number according to need. In the example shown in FIG. 2, component parts A and component part B are slender rods, and are alternately gathered into an aggregate. Although in the example shown in FIG. 2 the component parts are rod shaped, the component parts may also have a small cubic or spherical shape instead of the rod shape, and may be alternately stacked on top of one another. The term "alternately gathered" means to cover not only a structure in which component parts lie so as to have a regularity, but also a structure in which component parts exist randomly.

The shortest distance between the first portion (a), in which the oxidoreductase is immobilized on the electroconductive base member and the second portion (b), in which the electron mediator is immobilized on the electroconductive base member but the oxidoreductase is not immobilized on the electroconductive base member is preferably less than or equal to 1.0 mm in at least a portion of the enzyme electrode, and is more preferably less than or equal to 0.8 mm, and even more preferably less than or equal to 0.5 mm, and particularly preferably less than or equal to 0.1 mm, in at least a portion of the enzyme electrode. Shorter distances between the first portion (a) and the second portion (b) are more preferable. Therefore, the first portion (a) and the second portion (b) may contact each other, unless one of the two portions completely covers the other portion.

The enzyme electrode according to the invention may be used as at least one of the anode electrode and the cathode electrode of a fuel cell. Specifically, the invention relates to a fuel cell that incorporates an enzyme electrode as described above as at least one of the anode electrode and the cathode electrode (namely, a bio fuel cell). The fuel used in the fuel cell according to the invention is a substance that serves as a substrate of the oxidation-reduction reaction on the enzyme used in the electrode. Specific examples of the fuel include alcohols such as methanol, ethanol, etc., aldehydes such as acetaldehyde, etc., carboxylic acids such as formic acid, acetic acid, etc., sugars such as glucose, fructose, etc., as well as other fuels. The fuel may be supplied into the system, in the form of, for example, an aqueous solution. The fuel cell according to the invention may have a conventional configuration, except for the enzyme electrode.

The fuel cell having the enzyme electrode of the invention may contain a coenzyme in the fuel solution to assist catalysis by the oxidoreductase. Examples of suitable coenzymes include nicotinamide adenine dinucleotide (whose oxidized form is termed NAD, and whose reduced form is termed NADH, and which is generally termed NAD/NADH as well), nicotinamide adenine dinucleotide phosphate (whose oxidized form is termed NADP, and whose reduced form is termed NADPH, and which is generally termed NADP/NADPH as well), cytochrome, quinones (e.g., pyrroloquinoline quinone), etc. Among these, particularly preferred are NAD/NADH and NADP/NADPH, which function as coenzymes for various enzymes (which are collectively termed NAD(P)/NAD(P)H as well). However, if the oxidoreductase does not need a coenzyme (the enzyme for use at the cathode electrode often does not need a coenzyme), the presence of the foregoing coenzyme in the fuel solution is not required.

If the enzyme electrode of the invention is used as an anode electrode, the reduced-form coenzyme is produced (the reduced-form electron mediator is produced in the case where no coenzyme is employed) by an enzymatic reaction in the first portion (a) of the anode electrode (i.e., the portion in which the oxidoreductase is immobilized on the electroconductive base member). In contrast, the reduced coenzyme is oxidized (the reduced electron mediator is oxidized in the case where no coenzyme is employed) to release electrons in the second portion (b) of the anode electrode (i.e., the portion in which the electron mediator is immobilized on the electroconductive base member but the oxidoreductase is not immobilized on the electroconductive base member). In contrast, if the enzyme electrode of the invention is used as a cathode electrode, the oxidized-form electron mediator is produced (the oxidized-form coenzyme is produced when a coenzyme is employed) by an enzymatic reaction in the first portion (a) of the cathode electrode, and the oxidized-form electron mediator is reduced (the coenzyme is reduced in the case where a coenzyme is employed) in the second portion (b) of the cathode.

The enzyme electrode of the invention, as described above, is characterized in that the location of the enzymatic reactions is separate from the location of the electron transfer reaction. For example, if the enzyme electrode is used as an anode electrode and NAD/NADH is used as a coenzyme, it is desirable that [NAD]>[NADH] (the brackets denote the concentration) in order improve the enzymatic reaction rate. In contrast, in order to improve the reaction rate of the electron transfer from NADH, it is desirable that [NADH]>[NAD]. However, in conventional enzyme electrodes, because the location of the enzymatic reactions and the location of the electron transfer reactions are not separate from each other, it is impossible to realize optimum NAD/NADH concentration at each of the reaction locations. In addition, if the amount of the enzyme immobilized in the conventional enzyme electrode is increased so as to improve the output, the enzymatic reaction rate improves, but the permeability and the electroconductivity of the electrode surface decline, giving rise to the following problem. Specifically, the action of the coenzyme or the electron mediator is inhibited, so that the rate of the electron transfer reaction for extracting electrons from the coenzyme or the electron mediator declines. In the enzyme electrode according to the invention, however, because the location of the enzymatic reaction is separate from the location of the electron transfer reaction, it is possible to, for example, improve the reaction rate of the electron transfer from NADH by rapidly oxidizing NADH at the location of the electron transfer reaction, while keeping the rate of the enzymatic reaction high at the location of the enzymatic reaction by maintaining the concentration balance of [NAD]>[NADH]. In addition, because it is not necessary to increase the amount of enzyme that is immobilized, the permeability or the electroconductivity of the electrode surface is not reduced. Therefore, a fuel cell that includes an enzyme electrode according to the invention as at least one of the anode electrode and the cathode electrode has a higher power output than a fuel cell that employs a conventional enzyme electrode.

Incidentally, the enzyme electrode of the invention may be used not only in fuel cells but also, for example, as an electrode for use in a bio-sensor. The enzyme electrode of the invention is advantageous in those uses because the enzyme electrode of the invention is able to achieve high power output even if the amount of enzyme provided is small.

The invention will be described more in detail below with reference to examples, but is not limited by the following examples.

1. Manufacture of Electrode

[1] Electrode 1

Related-Art Example

Procedure 1

Manufacture of Base Electrode 3 mg of an electroconductive carbon black, 13 μl of 10% PVP solution and 180 μl of NMP were mixed, and then were dispersed by sonication to form a carbon slurry. Details of the carbon slurry raw materials are as shown in Table 1.

TABLE 1

| Carbon slurry component | Remarks |
| --- | --- |
| Electroconductive carbon black | Ketjen black by Lion KK ground in an agate mortar was used |
| 10% PVP solution | 10% (w/v) solution of poly(4-vinylpyridine) (PVP) in N-methyl-2-pyrrolidone (NMP) |
| NMP | N-methyl-2-pyrrolidone |

The carbon slurry obtained as described above was impregnated into a carbon fiber mat having a diameter of 1 cm (Torayca Mat B0050 by Toray KK, having a thickness of 0.79 mm). The mat was then dried at 90° C. for 3 hours, thereby forming the base electrode.

Procedure 2

Immobilization of Enzyme

An enzyme-immobilizing solution having a composition shown in Table 2 was prepared. After the enzyme-immobilizing solution was impregnated into the base electrode, the base electrode was left standing to dry at 4° C. for 8 hours or longer.

TABLE 2

| | |
| --- | --- |
| 100 mg/ml FDH (formate dehydrogenase) from *C. boidinii* | 25 μl |
| 20% poly-L-lysine (dissolved in distilled water to 20% (w/v)) | 4.1 μl |
| 2.5% glutaraldehyde (commercially available 25% glutaraldehyde solution was diluted to 10 times with distilled water) | 4.4 μl |
| 10 mM Tris-HCl buffer (Trizma base was dissolved in distilled M water to make a 1M solution, which was then titrated with HCl) | 7.2 μl |
| 50 mg/ml BSA (bovine serum albumin) | 1.5 μl |
| Distilled water | 12.8 μl |
| Total | 55 μl |

Procedure 3

Adsorption of Mediator

The immobilized enzyme base-electrode was dipped in 400 μl of 0.8 mM aqueous solution of 1-methoxy-5-methyl-phenazium-methyl sulfate (mPMS by Dojin Chemical Research Institute). The base electrode was left standing in the solution at 4° C. for 3 hours, so as to obtain Electrode 1.

[2] Electrode 2

Comparative Example

Electrode 2 was obtained in substantially the same manner as Electrode 1, except that the foregoing enzyme immobilization of Procedure 2 was omitted.

[3] Electrode 3

Example

Procedure 1

Manufacture of Base Electrode 0.4 mg of an electroconductive carbon black, 16.1 of 10% PVP solution and 22.5 μl of NMP were mixed, and then were dispersed by sonication so as to obtain a carbon slurry. Details of the carbon slurry raw material are as shown in Table 1. A carbon fiber mat having a diameter of 1 cm (Torayca Mat B0050 by Toray KK, having a thickness of 0.79 mm) was pealed into eight sheets whose thickness was ⅛ of that of the original mat. The sheets were impregnated with the carbon slurry obtained as described. The carbon fiber sheets were then dried at 90° C. for 3 hours, thereby forming the base electrode.

Procedure 2

Immobilization of Enzyme

An enzyme-immobilizing solution as shown in Table 2 was prepared in ⅓ of the amount shown in Table 2. The enzyme-immobilizing solution was impregnated into three of the eight base electrodes that were created by the foregoing Procedure 1. Then, the three base electrodes were left standing to dry at 4° C. for at least 8 hours.

Procedure 3

Adsorption of Mediator

Of the eight base electrodes created by Procedure 1, the four base electrodes without the enzyme immobilized thereon were dipped in 400 μl of 0.8 mM aqueous solution of 1-methoxy-5-methyl-phenazium-methyl sulfate (mPMS by Dojin Chemical Research Institute), and were left standing at 4° C. for 3 hours.

Procedure 4

Assembly of Electrode

The three enzyme-immobilized base electrodes obtained in Procedure 2 and the four mediator-adsorbed base electrodes are alternately gathered as shown in FIG. 1 to obtain Electrode 3.

2. Chronoamperometric Measurement

Figure 3:
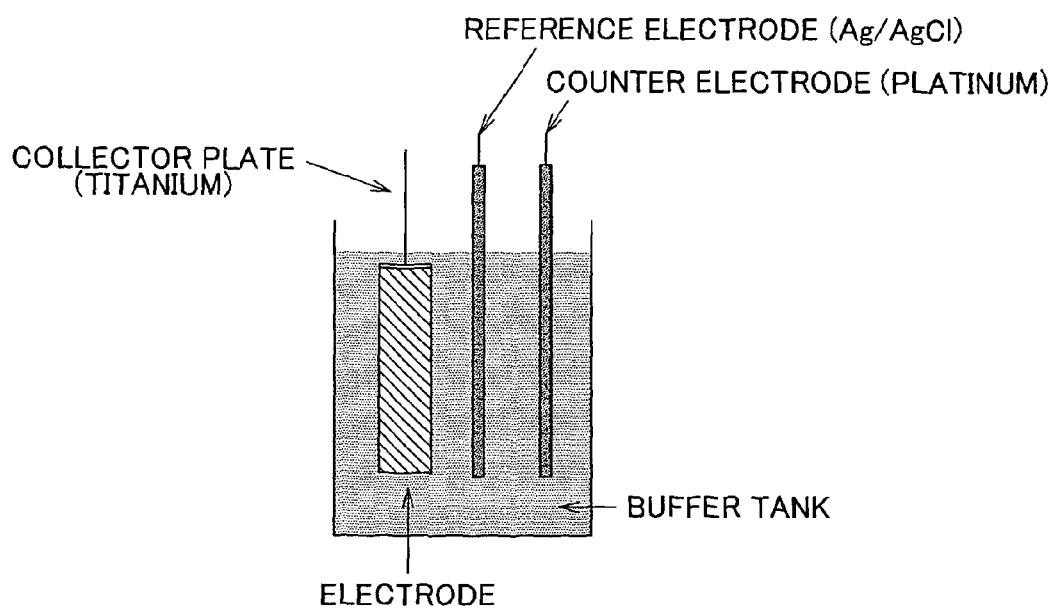
FIG. 3 is a schematic diagram of a chronoamperometric measurement device in an embodiment of the invention.

Using the apparatus shown in FIG. 3 and Model 2323 Bipotentiostat (by BAS Corporation), the performance of each electrode described above is measured through chronoamperometry (0.1 V).

Measurement 1

Output Based on 10 Mm NADH

Figure 4:
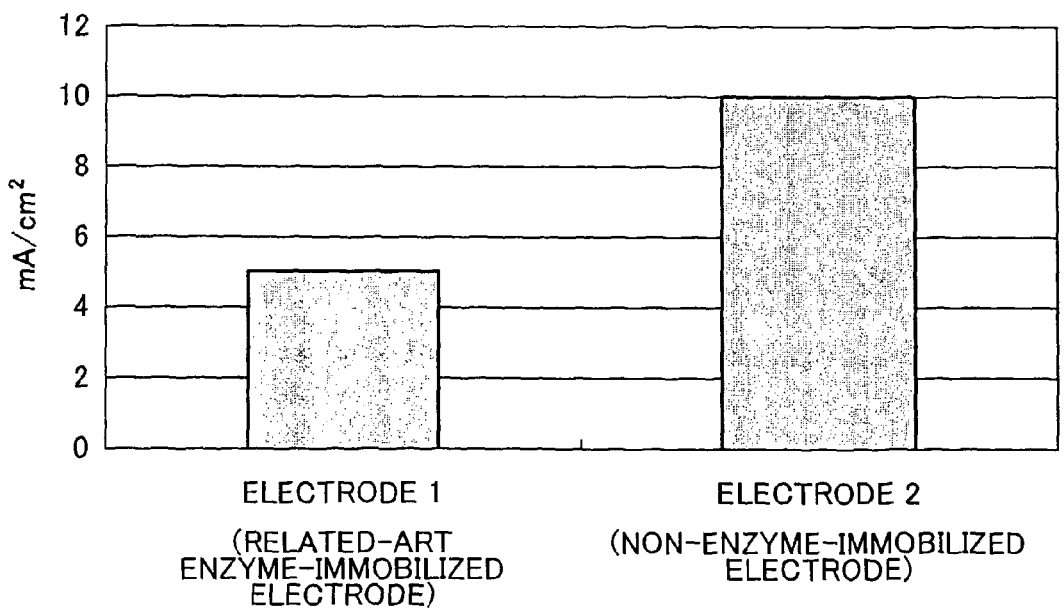
FIG. 4 is a graph showing results of measurement of the power outputs based on 10 mM NADH through the use of conventional electrodes with and without immobilized enzyme.

Using 1 M sodium phosphate buffer (pH 7.0) containing 10 mM of NADH, the initial currents of an arrangement that used Electrodes 1, which were related-art enzyme-immobilized electrodes, and of an arrangement that used Electrodes 2, which were electrodes without the enzyme immobilized thereon, were measured. Results of the measurement are shown in FIG. 4. The results indicate that the current obtained from a fixed concentration of NADH was lower with Electrodes 1, that is, the enzyme-immobilized electrodes, than with Electrodes 2, that is, the electrodes without the enzyme immobilized thereon. From this, it was predicted that the presence of an enzyme on the electrodes or a polymer used for the immobilization of the enzyme or the like would inhibit the electron transfer reaction.

Measurement 2

Output Based on Enzymatic Catalytic Reaction

Figure 5:
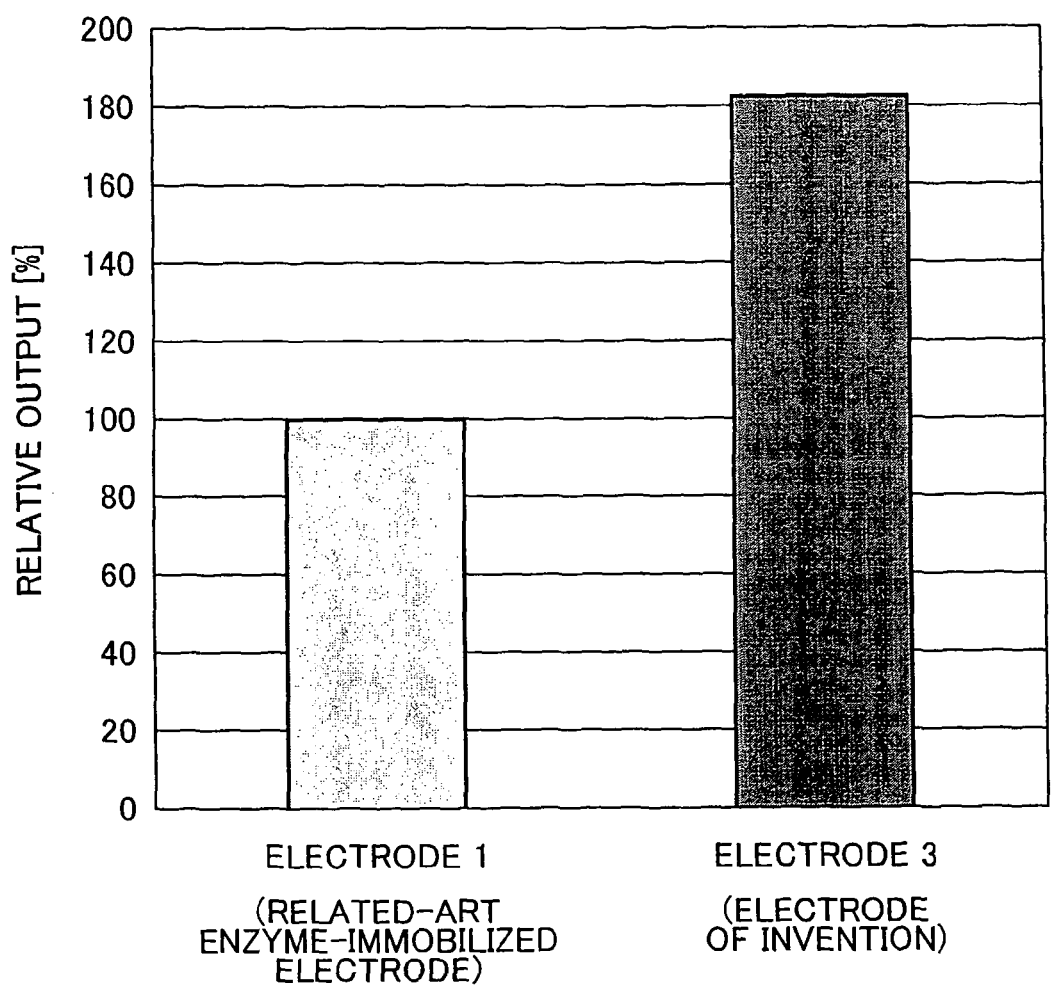
FIG. 5 is a graph showing results of measurement of the outputs based on an enzyme catalytic reaction, through the use of a conventional electrode with immobilized enzyme and an electrode according to the invention.

The power outputs based on enzymatic catalysis of conventional enzyme-immobilized electrodes (i.e., Electrodes 1), and electrodes according to the invention (i.e., Electrodes 3) were compared. The buffer used was an aqueous solution containing 25 mM NAD, 25 mM NADH, 0.34 M sodium formate, and 0.8 M sodium phosphate buffer (pH 7.0). Results of the measurement are shown in FIG. 5. The arrangement employing Electrodes 3, that is, the electrodes according to the invention in which enzyme-immobilized electrodes and non-enzyme-immobilized electrodes were alternately combined, achieved a relative output that was more than 1.8 times the output achieved by the arrangement employing Electrodes 1, that is, the related-art enzyme-immobilized electrodes.

The bio fuel cell, being a low-cost and low-environmental-load battery cell, has a possibility of being used as a replacement for the existing lithium ion battery cells. The bio fuel cells may be used as an electric power source for small electric vehicles and the like as well as medical appliances and mobile appliances. As for those uses, the scale of the market is very large.

While the invention has been described with reference to example embodiments thereof, it is to be understood that the invention is not limited to the described embodiments or constructions. To the contrary, the invention is intended to cover various modifications and equivalent arrangements. In addition, while the various elements of the example embodiments are shown in various combinations and configurations, other combinations and configurations, including more, less or only a single element, are also within the scope of the invention.

The invention claimed is:

1. A fuel cell comprising:
an enzyme electrode that incorporates a first electroconductive base member, a
second electroconductive base member, an oxidoreductase and an electron mediator; and
a fuel solution containing nicotinamide adenine dinucleotide as a coenzyme operable to assist the oxidoreductase, wherein
the enzyme electrode includes:
a first portion in which the oxidoreductase is immobilized on the first electroconductive base member;
and a second portion in which the electron mediator is immobilized but the oxidoreductase is not immobilized on the second electroconductive base member,
wherein the enzyme electrode includes a plurality of the first portions and a plurality of the second portions, and the first portions and the second portions are alternately gathered into an aggregate.

2. The fuel cell according to claim 1, wherein the first portion and the second portion is continuously alternate with each other.

3. The fuel cell according to claim 1,
wherein a shortest distance between the first portion and the second portion is less than or equal to 0.5 mm, in at least a portion of the enzyme electrode.

4. The fuel cell according to claim 1, wherein the fuel cell is configured to employ the enzyme electrode as at least one of an anode electrode and a cathode electrode.

5. The fuel cell according to claim 4, wherein:
the fuel cell is configured to employ the enzyme electrode as the anode electrode; and
a reduction starting potential of the electron mediator is greater than or equal to −0.32 V.

6. The fuel cell according to claim 4, wherein:
the fuel cell is configured to employ the enzyme electrode as the cathode electrode; and
a reduction starting potential of the electron mediator is less than or equal to 1.2 V.

7. The fuel cell according to claim 1, wherein
each of the first portions has a rod shape, and
each of the second portions has a rod shape.

* * * * *